United States Patent [19]

Ellis et al.

[11] 4,168,112

[45] Sep. 18, 1979

[54] CONTACT LENS WITH A HYDROPHILIC, POLYELECTROLYTE COMPLEX COATING AND METHOD FOR FORMING SAME

[75] Inventors: Edward J. Ellis, Rowley; Joseph C. Salamone, Marblehead, both of Mass.

[73] Assignee: Polymer Technology Corporation, Framingham, Mass.

[21] Appl. No.: 867,136

[22] Filed: Jan. 5, 1978

[51] Int. Cl.$^2$ .............................................. G02C 7/04
[52] U.S. Cl. .............................. 351/160 H; 427/164
[58] Field of Search .......................... 351/160, 160 H; 427/164

[56] References Cited

U.S. PATENT DOCUMENTS

| 3,560,424 | 2/1971 | Glaser et al. | 351/160 H |
| 3,963,662 | 6/1976 | Fujiwara et al. | 351/160 |

*Primary Examiner*—John K. Corbin
*Assistant Examiner*—Scott J. Sugarman
*Attorney, Agent, or Firm*—Wolf, Greenfield & Sacks

[57] ABSTRACT

Soft and hard contact lenses with an ionic charge on their surface are treated with a lens solution containing an oppositely charged ionic polymer to form a hydrophilic polyelectrolyte complex on the lens surface, which complex acts as a hydrogel and improves the properties of the lens.

13 Claims, No Drawings

CONTACT LENS WITH A HYDROPHILIC, POLYELECTROLYTE COMPLEX COATING AND METHOD FOR FORMING SAME

BACKGROUND OF THE INVENTION

It has long been known in the art that a contact lens must have surfaces that have a certain degree of hydrophilicity in order to be wet by tears thus providing unblurred vision.

Soft, hydrophilic contact lens, in addition to being wettable, provide comfort to the wearer but lack the ability to correct certain visual deficiencies such as astigmatism since they tend to conform to the shape of the corneal surface.

Often hydrophilic monomers can be added to a mixture of comonomers in the formation of contact lenses so that upon polymerization optically clear contact lenses result which have a certain degree of hydrophilicity. As the hydrophilic monomer content increases where it is added directly to the lens composition, the physical characteristics of the lenses are affected by the increased hydration propensity of the polymeric composition.

In some cases it has been known to treat a formed contact lens with a polymerizable hydrophilic monomer to form a surface coating of hydrophilic polymer grafted to an otherwise hydrophobic polymer surface. Although effective, this method of increasing the hydrophilic character of the lens surface can suffer from involved and difficult manufacturing procedures.

Present rigid and soft contact lenses sometimes retain water on their surfaces through secondary chemical bonding and as a consequence only a very thin layer of water molecules is present between the eye and the contact lens.

Soft lenses are inherently comfortable but oftentimes, as with hard lenses suffer from brief surface dryness between eye blinks. State of the art technology teaches that a water soluble neutral polymer may be applied to the surfaces of a hard contact lens to provide a "cushion" layer between the lens and the eye which is equated with increased wettability as well as wearer comfort and tolerance.

Dissipation of the "cushion" layer occurs rapidly in most prior art constructions, since there is little specific interaction between the mobile polymer in this layer and the lens surface. As a result the wearer begins to feel discomfort and must recoat the lens surfaces.

SUMMARY OF THE INVENTION

It is an object of this invention to provide a hard or soft synthetic polymer contact lens whose surface carries a thin layer of polyelectrolyte complex coating the lens surface and electrostatically bound thereto.

It is another object of this invention to provide a method of rendering a contact lens that has an ionic surface more compatible with the eye by immersing the lens in a solution of an oppositely charged ionic polymer to form a thin polyelectrolyte complex on the lens surface, which complex increases its hydrophilic character for a greater period of time relative to an untreated surface and which reduces the tendency for mucoproteins, a normal constituent of lacrimal tears, to adhere to a lens surface.

The layer or coating comprises a polyelectrolyte complex which is formed by reaction of an ionic lens surface with an oppositely charged ionic polymer, and this complex forms a hydrogel at the lens surface which absorbs water, has good water retention, and is compatible with the physiological structures of the eye. A durable "cushion" is formed which provides long lasting comfort to the eye.

In the preferred embodiment, the lens is an oxygen permeable hard lens which carries an ionic charge or has the potential of having an ionic charge. Preferably the lens coating is formed by merely immersing the lens in a solution which consists essentially of an ionic polymer dissolved in a water solution or a water solution containing soluble organic components comprising from 0.001 to 10% by weight of the solution. The ionic polymer can be any ionic polymer compatible with the eye and which does not cause eye irritation yet which forms a hydrogel and which is electrostatically bound to the surface of the contact lens.

It is a feature of this invention that thin coatings of from 20 to 2,500 Angstroms are formed, which coatings not only increase the compatibility of contact lens with the eye but also add a cushioning effect between the lens and the eye. Such coatings can avoid problems of punctate staining and further enhance the ability of the contact lens to be worn in the eye for periods up to 24 hours or more.

Depending on the concentration of ionic sites on the lens surface and the concentration of oppositely charged ionic polymer with which the surface is reacted, either wetting, soaking, or lubricating solutions can be prepared to provide optimal wearer comfortability. In addition, if cleaning agents are mixed with the ionic polymer solution, mucus, dirt and other unwanted deposits can be removed from the resulting polyelectrolyte complex surface.

DESCRIPTION OF PREFERRED EMBODIMENTS

Soft and hard synthetic polymer contact lens materials are normally prepared from neutral monomers and/or polymers. In this invention both soft and hard contact lens materials are prepared in such a manner that ionic sites are present on the lens surface, such sites can be reacted with a lens solution containing an oppositely charged, hydrophilic polymer. If the surface of the lens is considered polyanionic, the surface can then be reacted with a hydrophilic polycation with the resulting formation of a hydrophilic polyelectrolyte complex. Polyelectrolyte complexes have an equal amount of cations and anions, each obtained from a different source. In addition, these overall electrically neutral complexes exist as ionically cross-linked hydrogels that are effective in retaining water of hydration. In this invention, a surface coating of polyelectrolyte complex is achieved on a lens surface. A soft contact lens prepared entirely from a polyelectrolyte complex is known but would not have the desired properties of lenses preferred in accordance with this invention. In the present invention, it is possible that the reaction of ionic sites on a polymer surface, or potential ionic sites, with concommitant release of a low molecular weight electrolyte such as sodium chloride, hydrogen chloride, sodium sulfate, sodium methyl sulfate or any other related electrolyte could give rise to a monolayer coating of polyelectrolyte complex.

Polyelectrolyte complexes, although highly hydrophilic, are water-insoluble and can be dissolved with some difficulty usually by a ternary solvent system incorporating water, a water-soluble organic compound, and a low molecular weight electrolyte. This solubility behavior implies that in the present invention the polyelectrolyte complex treated surface is very difficult to dissolve and separate from the lens surface by the aqueous fluids of the eye, although this surface coating conceivably could be eroded by mechanical action in the eye during wear. Should dissipation of the polyelectrolyte complex from the lens surface occur, it can readily be replaced by retreatment of the lens with the appropriate oppositely charged polyion solution.

The polyelectrolyte complex on the lens surface can be achieved by several means. If an anionic surface is desired, this can be accomplished by incorporation into the lens formulation of any monomer or monomers from the acrylate or methacrylate salt group, a vinyl sulfonate salt, an allyl or methallyl sulfonate or sulfate salt, a styrene sulfonate salt, an acryloyloxy ethyl or methacryloyloxyethyl sulfate salt, a substituted acrylamido or methacrylamido sulfonate salt or from related phosphonate, phosphate and phosphite salts of polymerizable monomers. Alternatively, a potentially anionic surface can be generated for subsequent treatment with a polycation followed by elimination of a low molecular weight acid (such as hydrogen chloride) or by subsequent treatment with a neutral basic polymer resulting in an acid-base neutralization reaction. Such anionic monomers include compounds such as acrylic and methacrylic acid, vinylsulfonic acid, allyl or methallyl sulfonic or sulfuric acid, styrene sulfonic acid, an acrylamido or methacrylamido sulfonic acid, or a polymerizable phosphonic or phosphoric acid.

If a cationic surface is desired, this is accomplished by incorporation into the lens formulation of any quaternary or protonated monomer or monomers from the acrylate or methacrylate salt group, a vinylpyridinium salt, a vinylimidazolium salt, a vinylimidazolinium salt, a vinylthiazolium salt, a vinylbenzylammonium salt, a diallyldialkylammonium salt, or a related alkylated or protonated polymerizable sulfonium or phosphonium salt. Alternatively, a potentially cationic surface can be generated for subsequent treatment with a polyacid resulting in an acid-base neutralization reaction. Such potentially cationic monomers include compounds such as a dialkylaminoethyl acrylate or methacrylate, a vinylpyridine, a vinylimidazole, a vinylbenzyl amine, a vinyl alkyl ether or sulfide, or a polymerizable vinyl phosphine.

It is also possible to generate an ionic charge on the lens surface by chemically or electrically modifying a neutral monomeric repeat unit to one that is charged. For example, an anionic surface can be obtained by treating a polyester material, such as polymethylmethacrylate, with an aqueous base, such as sodium hydroxide, to yield sodium methacrylate units on the lens surface. Alternatively, a polyester material can be hydrolyzed with an acid to yield methacrylic acid units on the lens surface which function as potential anionic sites. Similarly, a cationic surface can be obtained by alkylating or protonating neucleophilic amine, sulfide or phosphine units on the lens surface.

Virtually all hard and soft contact lens materials presently disclosed are electrically neutral polymers or copolymers. Such materials can be modified to include ionic surface groups. One general method for all types of lenses would include treatment of the surface with high energy irradiation in the presence of air to generate ionic surface groups, see A. Chaprio, *Radiation Chemistry of Polymeric Systems*, Vol. XV, Interscience, New York, 1962, and F. A. Makhlis, *Radiation Physics and Chemistry of Polymers*, Wiley and Sons, New York, 1975.

Another method would include modification of polymeric lenses formulations through incorporation of ionic (or potentially ionic) monomers. Polymethyl methacrylate, which is currently the material of choice in the hard lens area, is amenable to such modification. Examples of this approach include the copolymerization of either acrylic acid, methacrylic acid or dimethylaminoethyl methacrylate to provide a polymethyl methacrylate lens with ionic groups on the surface.

Another example would include the modification of oxygen permeable lens formulations such as those in U.S. Pat. No. 3,808,178. These formulations are copolymers of methyl methacrylate with a siloxanyl alkyl ester of methacrylic acid and can be modified through the addition of either acrylic acid, methacrylic acid or dimethylaminoethyl methacrylate.

In a similar fashion the monomers acrylic acid, methacrylic acid or dimethylaminoethyl methacrylate could be employed as co-reactants with hydroxyethyl methacrylate to produce a material that is suitable for soft contact lenses which, in addition, provides an ionic surface.

Cellulosic polymers such as cellulose acetate butyrate have found use as contact lenses materials which exhibit moderate oxygen permeability. Polymers of this type contain residual cellulose alcohol functionalities which can be utilized as modification sites. Reaction of sodium chloroacetate with the alcohol functionalities will result in pendent carboxylate groups along the polymer chain. Contact lenses produced from this modified CAB material would be inherently wettable with an ionic surface receptive to polyelectrolyte complex formation.

The synthetic resin lens preferably has a total ionic charge of from 0.001% to 10%. Thus from 0.001% to 10% of the surface area is charged and the charge density often is about 5%.

The lens solutions of this invention are in all cases USP sterile, preferably water solutions containing ingredients common to lens solutions and which carry from 0.001 to 10% by weight of a water soluble ionic polymer or polymers such as:

Cationic homopolymers and copolymers of:
N,N-dimethylaminoethyl acrylate and methacrylate
2-methacryloyloxyethyltrimethylammonium chloride and methylsulfate
2-,4-, and 2-methyl-5-vinylpyridine
2-,4-, and 2-methyl-5-vinylpyridinium chloride and methylsulfate
N-(3-methacrylamidopropyl)-N,N-dimethylamine
N-(3-methacrylamidopropyl)-N,N,N-trimethylammonium chloride
1-vinyl- and 2-methyl-1-vinylimidazole
1-vinyl- and 2-methyl-1-vinylimidazolium chloride and methylsulfate
N-(3-acrylamido-3-methylbutyl)-N,N-dimethylamine
N-(3-acrylamido-3-methylbutyl)-N,N,N-trimethylammonium chloride
N-(3-methacryloyloxy-2-hydroxylpropyl)-N,N,N-trimethylammonium chloride
diallyldimethylammonium chloride and methysulfate
vinylbenzyltrimethylammonium chloride
cationic starch cationic cellulose
ionene polymers Anionic sodium carboxymethylcellulose
sodium carboxymethylhydroxyethylcellulose
sodium carboxymethylstarch
sodium carboxymethylhydroxyethylstarch
hydrolyzed polyacrylamide and polyacrylonitrile
homopolymers and copolymers of:
    acrylic and methacrylic acids
    sodium acrylate and methacrylate
    vinylsulfonic acid
    sodium vinylfulfonate
    p-styrenesulfonic acid
    sodium p-styrenesulfonate
    2-methacryloyloxyethylsulfonic acid
    3-methacryloyloxy-2-hydroxypropylsulfonic acid
    2-acrylamido-2-methylpropanesulfonic acid
    allylsulfonic acid
    2-phosphatoethyl methacrylate Other additives to the soaking lens solutions of this invention include conventional lens solution cleaning and soaking solution additives. Preservatives such as benzyalkonium chloride, ethylenediaminetetraacetic acid (EDTA), mercurials and chlorobutanol can be used. Wetting agents such as polyvinyl alcohol, hydroxypropyl methylcellulose and methyl cellulose can be used. Lubricating agents such as the wetting agents above but in known higher concentrations can be used. Soaking and cleaning agents such as neutral detergents including sodium dodecyl sulfate and neutral surfactants based on nonyl phenol can be used. Other conventional buffers, biocides and viscosity modifiers may also be used. The additives are used in a wide range of concentrations as known in the art. Preferably the pH of the solutions are as near to body pH as possible and always in the range of pH 6-8.

While it is preferred to merely soak the lens in the solution at room temperature, the solution can also be sprayed, dropped, or rubbed on the lens surface.

In all cases it is preferred to form a coating of no more than 2,500 Å over the lens surface which acts as a hydrogel. The hydrogel formed by the polyelectrolyte complex is an ionically crosslinked polymer that absorbs large amounts of water and at least 10% of its own weight of water. The lenses tend to be nonirritating to the eye and can be worn for long periods of time.

Specific examples of this invention are given below but are not meant in any way to limit this invention.

EXAMPLE I

Hard polymeric test samples were prepared from methylmethacrylate (MMA) and also from a comonomer mixture of methyl methacrylate (MMA) and methacrylic acid (MA). A minor amount of tetraethyleneglycol dimethacrylate (TEGDM) was incorporated in both formulations as a crosslinking agent. The free radical initiator 2,2'-azobisisobutyronitrile(AIBN) was utilized to effect polymerization. The formulation components (shown in Table I in weight percent) were thoroughly mixed, transferred to test tubes, stoppered, degassed, then filled with nitrogen. The test tubes were placed in a water bath at 40° C. and allowed to polymerize for two days. The tubes were then placed in a 60° C. oven for an additional three days, after which the polymerized rods were removed from the tubes. The rods were then subjected to conditioning for approximately fifteen hours at 100° C. under vacuum to complete the polymerization process and relieve any mechanical stresses present. Test specimens, in the form of 3/16" by ½" discs, were machined from the conditioned rods. The flat machined surfaces of the discs were then highly polished to provide an appropriate surface for contact angle measurements.

Contact angles were determined on hydrated specimens after immersed in $H_2O$ for 2 days with the values representing the advancing water droplet angle on the polished surface. Lower angles are indicative of more wettable materials which can be attributed to a more polar surface either as a result of the chemical groups present or the presence of bound water molecules.

The significantly lower contact angle produced by surface treatment "B" clearly illustrates the embodiment of this invention. The cationic hydroxyethylcellulose is ionically bound to the surface carboxylate (anionic) groups producing a layer of polyelectrolyte complex which contains bound water.

TABLE I

| Composition (wt. percent reagent) | | | | Surface Treatment | Advancing Angle in degrees |
|---|---|---|---|---|---|
| MMA | MA | TEGDM | AZO | | |
| 98.8 | — | 1.0 | 0.2 | none | 82–84 |
| 93.8 | 5 | 1.0 | 0.2 | none | 74–75 |
| 93.8 | 5 | 1.0 | 0.2 | A* | 77–78 |
| 93.8 | 5 | 1.0 | 0.2 | B** | 64–65 |

*Treatment "A" was a five minute immersion in a sodium carbonate water solution (pH = 10.7) followed by a thorough rinse with distilled water.
**Treatment "B" was initially identical to treatment "A" with a subsequent five minute immersion in a 0.1 weight percent cationic hydroxyethylcellulose (Union Carbide JR-125 resin) water solution at room temperature followed by a thorough rinse with distilled water.

EXAMPLE II

Using the experimental procedures described in Example I hard polymeric test samples were prepared from methyl methacrylate (MMA), methacryloyloxypropyl tris(trimethylsilyl) siloxane (TRIS) and methacrylic acid (MA). A minor amount of tetraethylene glycol dimethacrylate (TEGDM) was incorporated as a crosslinking agent. The free radical initiator 2,2'-azobisisobutyronitrile (AIBN) was utilized to effect polymerization. The concentration of reagents employed, surface treatments and contact angle values are presented in Table II. This particular formulation was chosen as typical of those presently utilized in the production of hard, oxygen permeable contact lenses.

The lower contact angles exhibited by samples when surface treated by method "B" or "C" demonstrates the applicability of this invention to polymeric materials suited for hard, oxygen permeable contact lens.

TABLE II

| Composition (wt. percent reagent) | |
|---|---|
| MMA | 59.4 |
| TRIS | 34.6 |
| MA | 4.9 |
| TEGDM | 0.9 |
| AZO | 0.2 |
| Surface Treatment | Advancing angle in degrees |
| none | 80–82 |
| "A" | 82–83 |
| "B" | 77–78 |

TABLE II-continued

| "C"* | 78-79 |
|---|---|

*Treatment "C" was initially identical to treatment "A" with a subsequent five minute immersion in a 0.1 weight percent polyvinylbenzyl trimethyl ammonium chloride water solution followed by a thorough rinse with distilled water.

EXAMPLE III

Using the experimental procedures described in Example I hard polymeric test samples were prepared from methyl methacrylate (MMA), methacryloyloxypropyl tris(trimethylsilyl) siloxane (TRIS) and dimethylaminoethyl methacrylate (DMAEM). A minor amount of tetraethylene glycol dimethacrylate (TEGDM) was incorporated as a crosslinking agent. The free radical initiator 2,2'-azobisisobutyronitrile(AIBN) was utilized to effect polymerization. The concentration of reagents employed, surface treatments and contact angle values are presented in Table III. This particular composition was chosen as typical of a material which could be utilized in the production of highly oxygen permeable, hard contact lenses.

This example illustrates the incorporation of a cationic monomer in the polymer formulation which is receptive to treatment with an anionic polymer to form a surface layer of polyelectrolyte complex. This behavior demonstrates the versatility of the present invention in that either an anionic (Examples I and II) or a cationic (Example III) monomer may be incorporated into a polymeric formulation which is capable of forming a polyelectrolyte complex with a polyion of the opposite charge.

TABLE III

| Composition (wt. percent reagent) | |
|---|---|
| MMA | 51.8 |
| TRIS | 42.4 |
| DMAEM | 4.7 |
| TEGDM | 0.9 |
| AZO | 0.2 |
| Surface Treatment | Advancing angle in degrees |
| none | 83-84 |
| "D"* | 84-85 |
| "E"** | 75-76 |
| "F"*** | 77-78 |

*Treatment "D" was a five minute immersion in a hydrochloric acid solution (pH = 3.0) followed by a thorough rinse with distilled water.
**Treatment "E" was a five minute immersion in a 0.1 weight percent polyacrylic acid water solution followed by a thorough rinse with distilled water.
***Treatment "F" was initially identical to treatment "D" with a subsequent five minute immersion in a 0.1 weight percent sodium polystyrenesulfonate water solution followed by a thorough rinse with distilled water.

In general, the polymeric material of the lens is preferably selected from the group comprising:

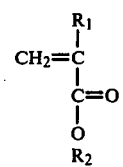

where $R_1 =$ H, $CH_3$, $CH_2COOH$, $CH_2COOCH_3$, or $CH_2COOC_6H_5$, and $R_2 =$ H, or $C_1$-$C_{20}$ derivative of a monohydric alkanol, a $C_1$-$C_3$ derivative of dihydric and trihydric alkanols, or

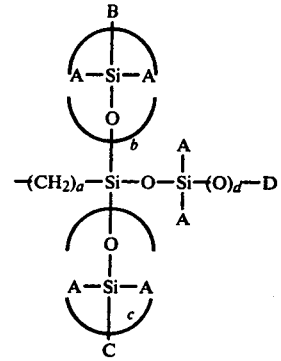

where "a" is an integer from one to three, "b" and "c" are integers from zero to two, "d" is an integer from zero to one, A is selected from the class of methyl and phenyl groups, B is selected from the class of methyl or phenyl groups, C and D represent either no group (cyclic ring from "c" to "d") or methyl or phenyl groups.

The polymeric material can also consist essentially of:

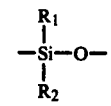

where $R_1$ and $R_2$ are selected from H, $CH_3$, $C_2H_5$, $C_3H_7$, $C_6H_5$, COOH, $CH_2=CH-$ and $-O-$ groups.

In some cases, the polymeric material consists essentially of cellulose units having the formula:

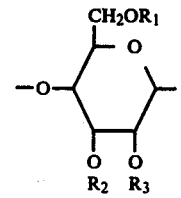

where $R_1$, $R_2$ and $R_3$ are selected from H, derivatives of $C_1$-$C_{20}$ carboxylic acid, $C_1$-$C_{20}$ alkyl groups, $C_1$ to $C_3$ monohydric and dihydric alkanols, phenyl groups, $CH_2COOH$, and $CH_2CH_2N^+R_3$ groups wherein $R_4=$ H, $CH_3$, or $C_2H_5$.

While specific polymers described can be used alone, they can also be used in combination with each other. For example, the lens composition can comprise a mixture of two or more different derivatives of acrylic or methacrylic acid. It is important that the ionic charge be present and that the polymer or polymer mixture provide good contact lens characteristics as known in the art such as optical clarity.

Preferably the contact lenses have a lens surface which contain ionic sites which are complexed to oppositely charged polymer sites selected from the groups COOX, $SO_3X$, and $PO_3X$, wherein X=H or monovalent inorganic ion, $N^+(R)_3$ groups, wherein R=H, $CH_3$ or $C_2H_5$ groups, $S^+(R')_2$, wherein R'=H, $CH_3$, or $C_2H_5$ groups, $P^+(R'')_3$, wherein R''=H, $CH_3$, $C_2H_5$ and phenyl groups, pyridinium groups and imidazolium groups.

what is claimed is:

1. A contact lens comprising an optically clear, transparent body having a lens surface,
said lens surface defining a polymeric material carrying an ionic charge,
a thin layer of a polyelectrolyte complex coating said lens surface and electrostatically bound thereto,
said coating comprising an ionic polymer and said polymer forming a hydrogel at the surface which absorbs water, has good water retention and is compatible with the physiological structure of the eye.

2. A contact lens in accordance with claim 1 wherein said polymeric material is:

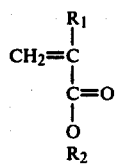

where $R_1 = H$, $CH_3$, $CH_2COOH$, $CH_2COOCH_3$, or $CH_2COOC_6H_5$, and $R_2 = H$, or $C_1-C_{20}$ derivative of a monohydric alkanol, a $C_1-C_3$ derivative of dihydric and trihydric alkanols, or

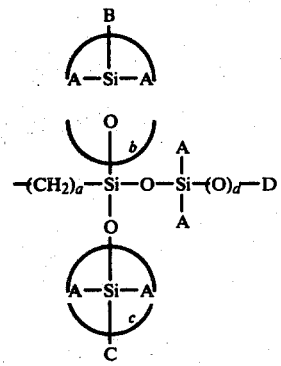

where "a" is an integer from one to three, "b" and "c" are integers from zero to two, "d" is an integer from zero to one, A is selected from the class of methyl and phenyl groups, B is selected from the class of methyl or phenyl groups, C and D represent either no group (cyclic ring from "c" to "d") or methyl or phenyl groups.

3. A contact lens in accordance with claim 2 wherein said lens surface contains ionic sites which are complexed to oppositely charged polymer sites selected from the groups COOX, $SO_3X$, and $PO_3X$, wherein X=H or monovalent inorganic ion, $N^+(R)_3$ groups, wherein R=H, $CH_3$ or $C_2H_5$ groups, $S^+(R')_2$, wherein $R'$=H, $CH_3$, or $C_2H_5$ groups, $P^+(R'')_3$, wherein $R''$=H, $CH_3$, $C_2H_5$ and phenyl groups, pyridinium groups and imidazolium groups.

4. A contact lens in accordance with claim 1 and further comprising said polymeric material consisting essentially of

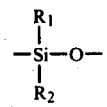

where $R_1$ and $R_2$ are selected from H, $CH_3$, $C_2H_5$, $C_3H_7$, $C_6H_5$, COOH, $CH_2$=CH— and —O— groups.

5. A contact lens in accordance with claim 4 wherein said lens surface contains ionic sites which are complexed to oppositely charged polymer sites selected from the groups COOX, $SO_3X$, and $PO_3X$, wherein X=H or monovalent inorganic ion, $N^+(R)_3$ groups, wherein R=H, $CH_3$ or $C_2H_5$ groups, $S^+(R')_2$, wherein $R'$=H, $CH_3$, or $C_2H_5$ groups, $P^+(R'')_3$, wherein $R''$=H, $CH_3$, $C_2H_5$ and phenyl groups, pyridinium groups and imidazolium groups.

6. A contact lens in accordance with claim 1 and further comprising said polymeric material consisting essentially of cellulose units having the formula

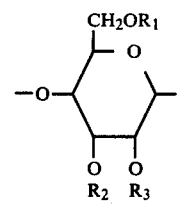

where $R_1$, $R_2$ and $R_3$ are selected from H, derivatives of $C_1-C_{20}$ carboxylic acid, $C_1-C_{20}$ alkyl groups, $C_1$ to $C_3$ monohydric and dihydric alkanols, phenyl groups, $CH_2COOH$, and $CH_2CH_2N^+R_3$ groups, wherein $R_4$=H, $CH_3$, or $C_2H_5$.

7. A contact lens in accordance with claim 6 wherein said lens surface contains ionic sites which are complexed to oppositely charged polymer sites selected from the groups COOX, $SO_3X$, and $PO_3X$, wherein X=H or monovalent inorganic ion, $N^+(R)_3$ groups, wherein R=H, $CH_3$ or $C_2H_5$ groups, $S^+(R')_2$, wherein $R'$=H, $CH_3$, or $C_2H_5$ groups, $P^+(R'')_3$, wherein $R''$=H, $CH_3$, $C_2H_5$ and phenyl groups, pyridinium groups and imidazolium groups.

8. A contact lens in accordance with claim 1 wherein said lens surface contains ionic sites which are complexed to oppositely charged polymer sites selected from the groups COOX, $SO_3X$, and $PO_3X$, wherein X=H or monovalent inorganic ion, $N^+(R)_3$ groups, wherein R=H, $CH_3$ or $C_2H_5$ groups, $S^+(R')_2$, wherein $R'$=H, $CH_3$, or $C_2H_5$ groups, $P^+(R'')_3$, wherein $R''$=H, $CH_3$, $C_2H_5$ and phenyl groups, pyridinium groups and imidazolium groups.

9. A contact lens in accordance with claim 1 wherein said lens surface has a total ionic charge of from 0.001% to 10%.

10. A contact lens in accordance with claim 9 wherein said thin layer of polyelectrolyte complex coating has a thickness in the range of from 20 to 2,500 Angstroms.

11. A contact lens in accordance with claim 10 wherein said lens surface contains ionic sites which are complexed to oppositely charged polymer sites selected from the groups COOX, $SO_3X$, and $PO_3X$, wherein X=H or monovalent inorganic ion, $N^+(R)_3$ groups, wherein R=H, $CH_3$ or $C_2H_5$ groups, $S^+(R')_2$, wherein $R'$=H, $CH_3$, or $C_2H_5$ groups, $P^+(R'')_3$, wherein $R''$=H, $CH_3$, $C_2H_5$ and phenyl groups, pyridinium groups and imidazolium groups.

12. A method of forming a polyelectrolyte complex coating on a polymeric contact lens, said method comprising,
providing said lens with a surface carrying an ionic charge,
wetting said lens surface with a wetting solution carrying an ionic polymer to form a thin layer of said polyelectrolyte complex electrostatically bound to said surface, said coating comprising an ionic polymer and said polymer forming a hydrogel at said surface which absorbs water, has good water retention and is compatible with the physiological structure of the eye.

13. A method in accordance with the method of claim 12 wherein said ionic polymer is in a water solution with said ionic polymer being present in an amount of from 0.001 to 10% by weight of said solution.

* * * * *